United States Patent [19]

Bays

[11] Patent Number: 5,796,188
[45] Date of Patent: Aug. 18, 1998

[54] BATTERY-POWERED MEDICAL INSTRUMENT WITH POWER BOOSTER

[75] Inventor: F. Barry Bays, Clearwater, Fla.

[73] Assignee: Xomed Surgical Products, Inc., Jacksonville, Fla.

[21] Appl. No.: 539,459

[22] Filed: Oct. 5, 1995

[51] Int. Cl.$^6$ .................... H02K 7/14; F02M 9/00
[52] U.S. Cl. .................. 310/50; 310/47; 310/40 MM; 606/180; 429/9; 429/149; 429/628
[58] Field of Search ............... 310/47, 40 MM, 310/50; 606/180; 429/9, 149, 156, 160, 168, 121, 123, 150, 178, 180, 628; 439/188, 500, 628

[56] References Cited

U.S. PATENT DOCUMENTS

| | | | |
|---|---|---|---|
| 3,173,417 | 3/1965 | Horner | 128/305 |
| 3,210,847 | 10/1965 | Prüfer | 32/27 |
| 4,149,530 | 4/1979 | Gow | 128/36 |
| 4,644,952 | 2/1987 | Patipa et al. | 128/305 |
| 5,076,805 | 12/1991 | Welch | 439/568 |
| 5,177,424 | 1/1993 | Connors | 320/2 |
| 5,214,353 | 5/1993 | Nilssen | 315/33 |
| 5,249,583 | 10/1993 | Mallaby | 128/754 |
| 5,296,315 | 3/1994 | Rein | 429/100 |
| 5,378,552 | 1/1995 | Dixon | 429/91 |
| 5,478,093 | 12/1995 | Eibl et al. | 279/51 |

OTHER PUBLICATIONS

"REDI" BUR System, Micromed Development Corporation, 1 page, 1994.
"Richards Improved MDS (Microsurgery Drill System)," Richards Medical Company, one page, 1900 or earlier.
"Micro Drill Power Systems," Xomed, Inc., one page, 1990 or earlier.
"Skeeter Ultra–Lite Oto–Tool Systems," Treace Medical, Inc., one page, 1988.
"Light and Precise, New Shea Micro Drill," Treace Medical, Inc., pp. 26A–26D, 1985.

Primary Examiner—Steven L. Stephan
Assistant Examiner—Timothy A. Williams

[57] ABSTRACT

A medical instrument, such as a surgical drill, includes a battery-powered handpiece and a booster. The handpiece includes an electrical device, such as a motor, having an operating characteristic responsive to changes in DC voltage and a battery that applies a first DC voltage to the electrical device. The booster is disposed externally of the handpiece body and includes a DC power source and a cable for connecting the DC power source with the battery in the handpiece to apply a second DC voltage to the electrical device. The operating characteristic of the electrical device, e.g., speed, is modified by selectively coupling or decoupling the booster from the handpiece.

16 Claims, 6 Drawing Sheets

BATTERY-POWERED MEDICAL INSTRUMENT WITH POWER BOOSTER

BACKGROUND OF THE INVENTION

1. Field of the Invention

The present invention relates to medical instruments and, more particularly, to battery-powered medical instruments incorporating electrical devices responsive to changes in applied voltage, such as hand-held surgical drills.

2. Discussion of the Prior Art

When using electrically operated medical instruments, such as surgical drills, there is frequently a need to modify an operating characteristic of the instrument such as speed, torque or power and/or to operate the instrument when a primary power source fails.

In the case of battery-operated medical instruments, a plurality of batteries may be needed to achieve a desired operating characteristic, adding to the space and bulk required in a handpiece of the medical instrument. A further disadvantage of battery-operated medical instruments is that the batteries can wear down or dissipate over time, increasing the risk of power loss during a medical procedure.

Electrically operated medical instruments can be powered by an external power source via wires; however, the constant presence of wires leading from the instrument to the power source can interfere with certain hand movements during medical procedures thereby limiting maneuverability and making delicate surgical procedures more difficult.

SUMMARY OF THE INVENTION

Accordingly, it is a primary object of the present invention to overcome the above mentioned problems and disadvantages of prior art battery-powered medical instruments.

It is another, more specific, object of the present invention to permit selective modification of the operating characteristics of an electrical device disposed within a handpiece of a battery-powered medical instrument without substantially increasing the complexity, cost or size of the handpiece.

It is a further object of the present invention to modify the operating characteristics of an electrical device disposed within a handpiece of a battery-powered medical instrument by connecting an external power source with a battery disposed in the handpiece to increase the voltage applied to the electrical device.

The present invention has an additional object to increase the speed of an electrical motor disposed within a handpiece of a battery-powered medical instrument, such as a surgical drilling apparatus, by connecting an external power source in series with a battery disposed in the handpiece to increase the voltage applied to the motor.

Some of the advantages of the present invention over the prior art are that the handpiece of the medical instrument can be powered by an internal battery and used alone when a first operating characteristic is required or with a booster attached when a second operating characteristic is required, that such a booster is useful for back-up power in the event the battery in the handpiece becomes partially or fully discharged, and that either or both of the handpiece and booster of the medical instrument can be made disposable for single patient use or sterilizable for reuse.

The present invention is generally characterized in a medical instrument including a handpiece with a body, an electrical device disposed within the body and having an operating characteristic responsive to DC voltage, a first battery disposed within the body for applying a first DC voltage to the electrical device, and a booster disposed externally of the body, the booster including a DC power source and means for connecting the DC power source with the first battery to apply a second DC voltage to the electrical device. In a preferred embodiment, the DC power source of the booster is a second battery connected in series with the first battery by the connecting means.

Another aspect of the present invention is generally characterized in a method of performing a medical procedure including the steps of applying a first voltage to an electrical device disposed within a handpiece of a medical instrument using a first battery disposed within the handpiece, generating a first output from the electrical device in response to the first voltage, connecting a second battery disposed outside the handpiece with the first battery to apply a second voltage to the electrical device and generating a second output from the electrical device in response to the second voltage. In a preferred embodiment, the first and second outputs are used in performing the medical procedure. For example, if the medical device is a motor, the first and second outputs can be first and second speeds of the motor, and a cutting member can be attached to the motor via a drive shaft for performing delicate procedures at the first speed using only the first battery and more aggressive procedures at the second speed using both the first and second batteries.

Other objects and advantages of the present invention will become apparent from the following description of the preferred embodiments taken in conjunction with the accompanying drawings, wherein like parts in each of the several figures are identified by the same reference characters.

DETAILED DESCRIPTION OF THE PREFERRED EMBODIMENTS

The medical instrument of the present invention is described hereinafter as a battery-powered surgical drilling apparatus for use in otologic procedures such as stapedectomies and tympanoplasties. It will be appreciated, however, that the medical instrument of the present invention can be embodied in any type of hand-held medical apparatus powered by a battery including, but not limited to, medical apparatus having motors for driving implements such as drills and screwdrivers, pumps for providing irrigation and aspiration at surgical sites, resistive elements for cauterizing tissue and light generating components for illumination and/or cutting.

Figure 1:
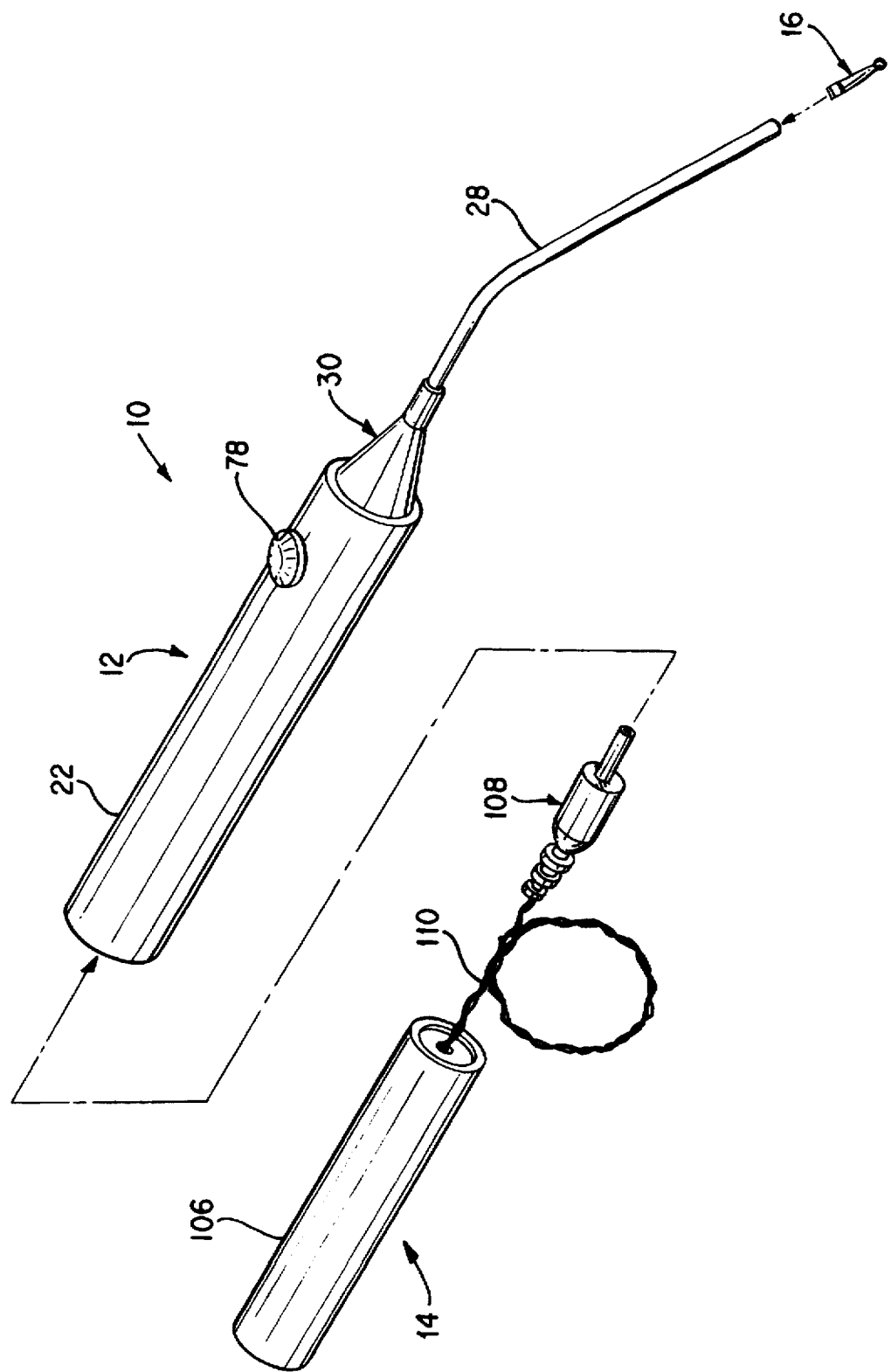
FIG. 1 is an exploded perspective view of a surgical drilling apparatus according to the present invention showing a handpiece, booster and cutting tip.
Figure 2:
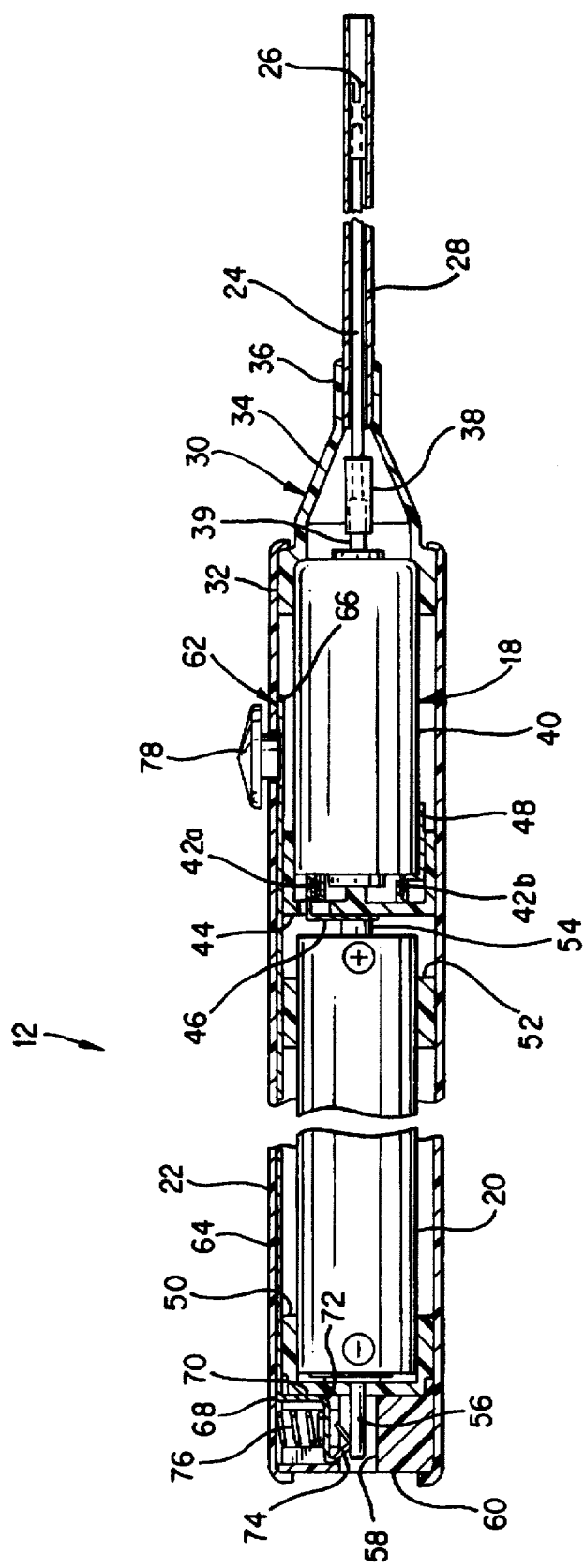
FIG. 2 is a side view, partly in section, of the handpiece shown in FIG. 1.
Figure 3:
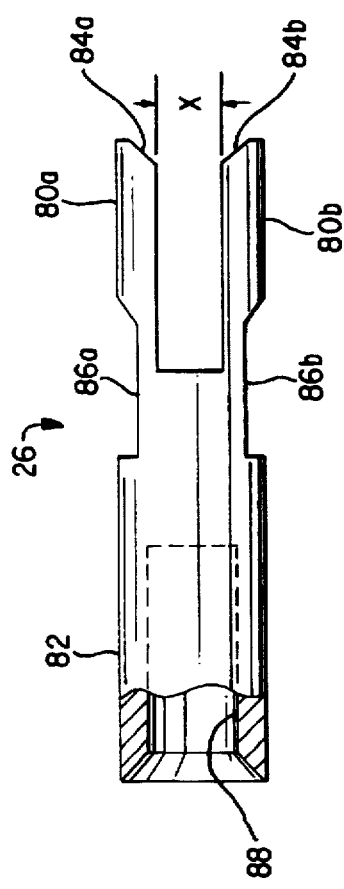
FIG. 3 is a side view, partly in section, of a collet for use in the handpiece of a surgical drilling apparatus according to the present invention.

A medical instrument according to the present invention, as illustrated in FIGS. 1–3, is embodied in a surgical drilling apparatus 10 having a handpiece 12, a booster 14 and a cutting tip or burr 16. As best seen in FIG. 2, handpiece 12 includes an electrical motor 18 and battery 20 disposed within a hollow cylindrical body 22 and an elongate drive shaft 24 extending distally from the motor to a collet 26 disposed within a stainless steel tube 28 outside the body. A plastic nose cone 30 couples a proximal end of tube 28 with a distal end of body 22 and includes a hollow cylindrical base 32 telescopically fitted within the body 22 adjacent a forward driving end of motor 18 and a hollow frustoconical portion 34 outside the body that tapers inwardly in a distal direction from the base to a second hollow cylindrical portion 36 of smaller diameter than the base. Tube 28 can be straight or angled as shown, and the proximal end of tube 28 is mounted within the second cylindrical portion 36 of the nose cone so that manual rotation of the nose cone about the longitudinal axis of the body will affect the position of the tube. Drive shaft 24 is flexible and is preferably formed of stainless steel cable coated with nylon to follow the shape of tube 28 and to reduce friction caused by movement of the drive shaft within the tube. A conventional coupling 38 connects the drive shaft 24 with a spindle 39 at the forward driving end of the motor 18.

Electrical motor 18 can be any type of conventional direct-current or DC motor having a range of speeds suitable for driving a cutting tip or burr but is preferably a cylindrical motor with a conductive housing 40 and a pair of terminals 42a and 42b located at the rear of the housing, such as the model RF-N60CA-13110 motor distributed by Mabuchi Motor America Corporation of New York, N.Y. The motor 18 is mounted concentrically within the body 22 of the handpiece between the cylindrical base 32 of the nose cone and a plastic cup-like connector cap 44 longitudinally spaced from the base; and, since forward and rearward ends of the motor 18 are received within the nose cone 30 and connector cap 44, respectively, a small radial gap or clearance is maintained between the conductive housing 40 of the motor and the body 22 of the handpiece. A first conductor 46 is made of a strip of electrically conductive material, such as copper or a cold-rolled half-hard brass CD 260 alloy, and is formed to mate with motor terminal 42a and to extend longitudinally in a proximal direction from the terminal 42a through a hole in the connector cap 44 and to bend against the proximal face of the connector cap. A second conductor 48, made of the same or similar material as that of conductor 46, is formed to mate with motor terminal 42b and to wrap around the rearward end of the motor 18 to make electrical contact with the conductive housing 40 of the motor.

Battery 20 can have any configuration to fit within the body 22 of the handpiece and can have any voltage in accordance with a desired operating speed of the motor but is preferably a 3.5 volt lithium battery of cylindrical configuration, such as the model CR12600SET battery available from Sanyo Energy (U.S.A.) Corporation of Gainesville, Fla. The battery 20 is mounted concentrically within the body 22 of the handpiece between the connector cap 44 and a plastic pin housing 50 proximally spaced from the connector cap. The plastic pin housing 50 has a cup-like configuration with a recess for receiving and supporting the proximal end of the battery 20, while a plastic battery ring 52 serves as a spacer supporting the distal end of the battery near the connector cap. A positive terminal 54 of the battery 20 extends from the distal face of the battery to contact the first conductor 46 on the proximal face of the connector cap. A negative terminal 56 in the form of a stainless steel pin extends from the proximal face of the battery 20 through a hole in the pin housing 50 to be disposed concentrically within a cylindrical passage or receptacle 58 of greater diameter than the pin 56 formed in a plastic plug housing 60 at the proximal end of the body 22. A third conductor 62, made of a strip of conductive material such as the brass alloy mentioned above, is formed to have a longitudinal portion 64 contacting the body 22 and extending from a distal end 66 disposed alongside the motor housing 40 to a bend 68 joining the longitudinal portion with a transverse portion 70 laying against a proximal face of the pin housing 50. A second bend 72 joins the transverse portion 70 with a folded portion 74 disposed within a recess formed in the plug housing 60 alongside the receptacle 58 in which the pin 56 is disposed. The folded portion 74 is generally triangularly shaped with a flat side parallel to the longitudinal axis of the body and a corner opposite the flat side contacting the pin 56. A curved spring washer 76 is disposed within a cavity formed transversely through the plug housing 60 and is held in compression between the flat side of the folded portion 74 and the body 22 to force the corner of the folded portion against the pin to create a conductive path between the pin and the distal end of the conductor. The longitudinal portion 64 of the conductor 62 passes through a slot or opening formed at the periphery of the connector cap 44 and is cantilevered alongside motor housing 40. A plastic button 78 extends transversely through an opening in body 22 to couple with the conductor 62 near the distal end 66 of the longitudinal portion so that a force can be applied near the distal end of the longitudinal portion via the button to cause the distal end of the conductor to deflect inward toward the motor and to make electrical contact with the motor housing 40 thus completing the circuit and powering the motor.

Figure 4:
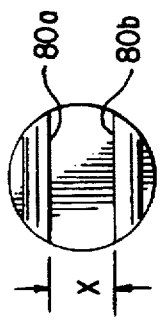
FIG. 4 is a front elevational view of the collet shown in FIG. 6.

Collet 26 is proximally spaced from the distal end of tube 28 and, as best seen in FIGS. 3 and 4, the collet includes a pair of laterally opposed jaws 80a and 80b at the distal end of a generally cylindrical base 82. Jaws 80a and 80b are generally parallel to one another and to a longitudinal axis of the collet but are bent toward one another slightly (e.g., about 0.007 inches) until separated by a predetermined gap x. A distal edge or corner 84a and 84b of each jaw adjacent the gap is chamfered or angled to widen the gap at the distal end of the collet thereby easing insertion of the cutting tip 16 as will be explained further below. Notches 86a and 86b are formed at respective junctions between the jaws 80a and 80b and the cylindrical base 82 and are sufficiently deep to permit slight bending of the jaws away from and towards one another under normal insertion pressures. A bore 88 formed at the proximal end of the cylindrical base 82 is configured to receive the drive shaft 24.

Figure 6:
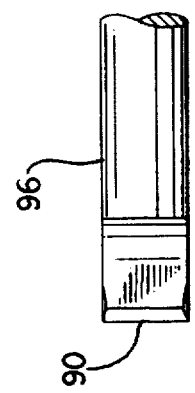
FIG. 6 is a top plan view of the cutting tip shown in FIG. 8.
Figure 5:
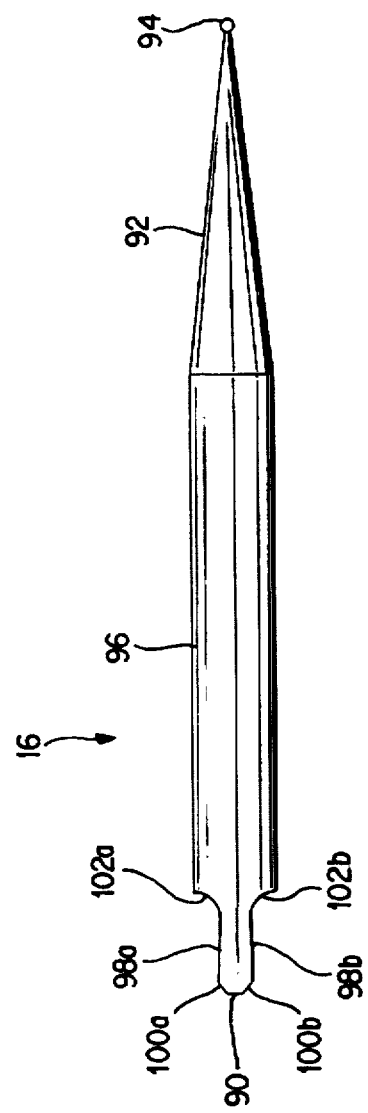
FIG. 5 is a side view of the cutting tip shown in FIG. 1.

Cutting tip 16, as shown in FIGS. 5 and 6, includes a notched proximal end 90, a tapered distal end 92 carrying a spherical burr 94, and a cylindrical shaft 96 extending between the notched proximal end 90 and the tapered distal end 92. Proximal end 90 is generally wedge-shaped with flat surfaces 98a and 98b on opposite sides of the wedge tapering slightly inward (e.g., at an angle of about 2°) in the direction of the cylindrical shaft 96. Surfaces 98a and 98b are laterally spaced from one another along their lengths a distance slightly greater than the distance x separating the jaws 80a and 80b of the collet (e.g., about 0.004 to about 0.005 inches greater than x) so that, when inserted between the jaws, the wedge-shaped proximal end of the tip will tend to separate the jaws and be held in compression therebetween. Chamfered edges 100a and 100b at respective proximal ends of the flat surfaces 98a and 98b help ease insertion, while fillet radii 102a and 102b at respective distal ends of the flat surfaces serve as stress reducing junctions between the flat surfaces and the cylindrical shaft. Burr 94 at the distal end of the tapered portion 92 is shown as a standard 1.0 mm diameter carbide but can have any shape or size dependent upon the procedure to be performed.

Figure 7:
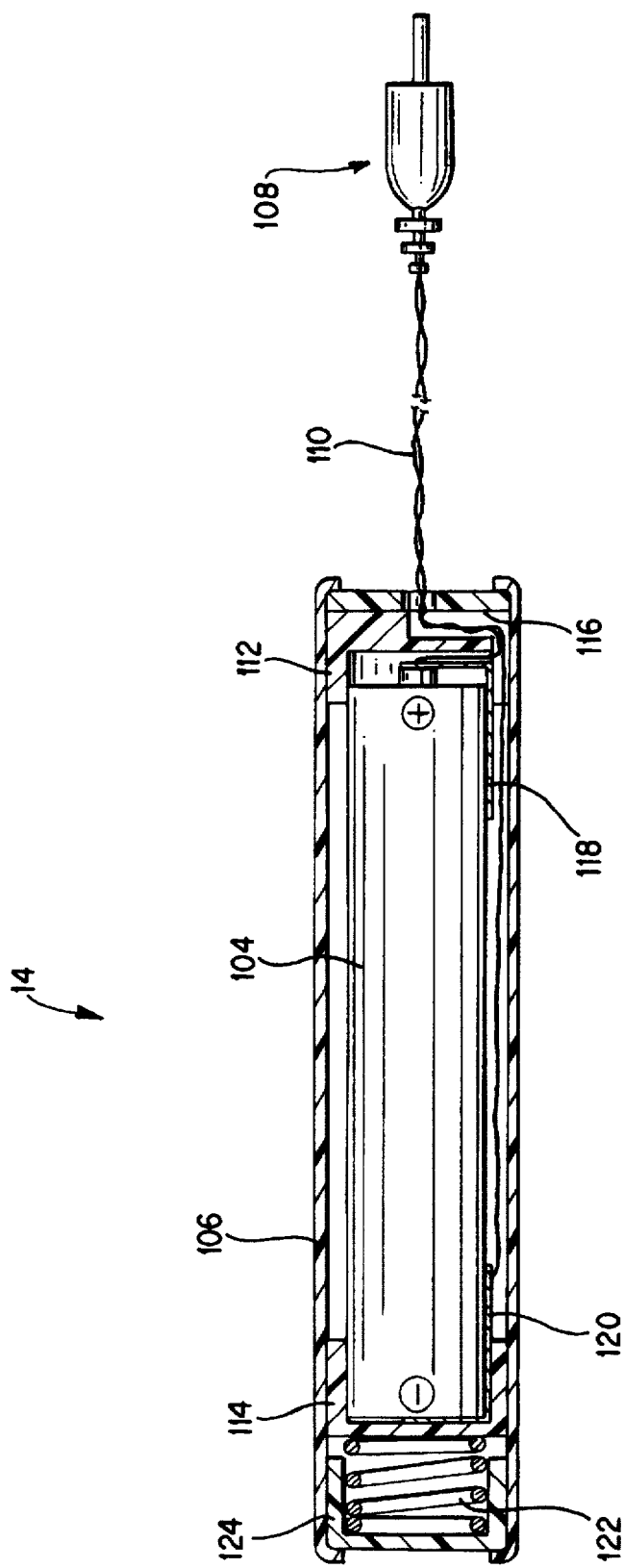
FIG. 7 is a side view, partly in section, of the booster shown in FIG. 1.

As best seen in FIG. 7, booster 14 includes a battery 104 disposed within a hollow cylindrical booster body 106 and a plug 108 disposed outside the booster body 106 and connected with the battery 104 via an electrical cable 110. Battery 104 can have any configuration to fit within the booster body 106 and any voltage in accordance with a desired operating speed of the motor but is preferably a 3.5 volt lithium battery like battery 20 within the handpiece 12. The battery 104 is mounted concentrically within the booster body 106 between a plastic wire cap 112 at the distal end of the booster body and a plastic booster cap 114 at the proximal end of the booster body. The wire cap 112 and booster cap 114 each have a cup-like configuration with a recess for receiving and supporting opposite ends of the battery 104. Wire cap 112 further includes an opening communicating with an aperture in a booster disc 116 that closes the distal end of the booster body. Electrical cable 110 includes a pair of twisted leads extending from a pair of L-shaped conductor strips 118 and 120 at the positive and negative terminals of the battery to the plug 108 via the opening in the wire cap 112 and the aperture in the booster disc 116. A stainless steel spring 122 is disposed within a recess formed in a second booster cap 124 proximally spaced from booster cap 114 and is held in compression between booster cap 114 and the second booster cap 124 to urge the positive and negative terminals of the battery 104 into contact with the conductor strips 118 and 120.

Figure 8:
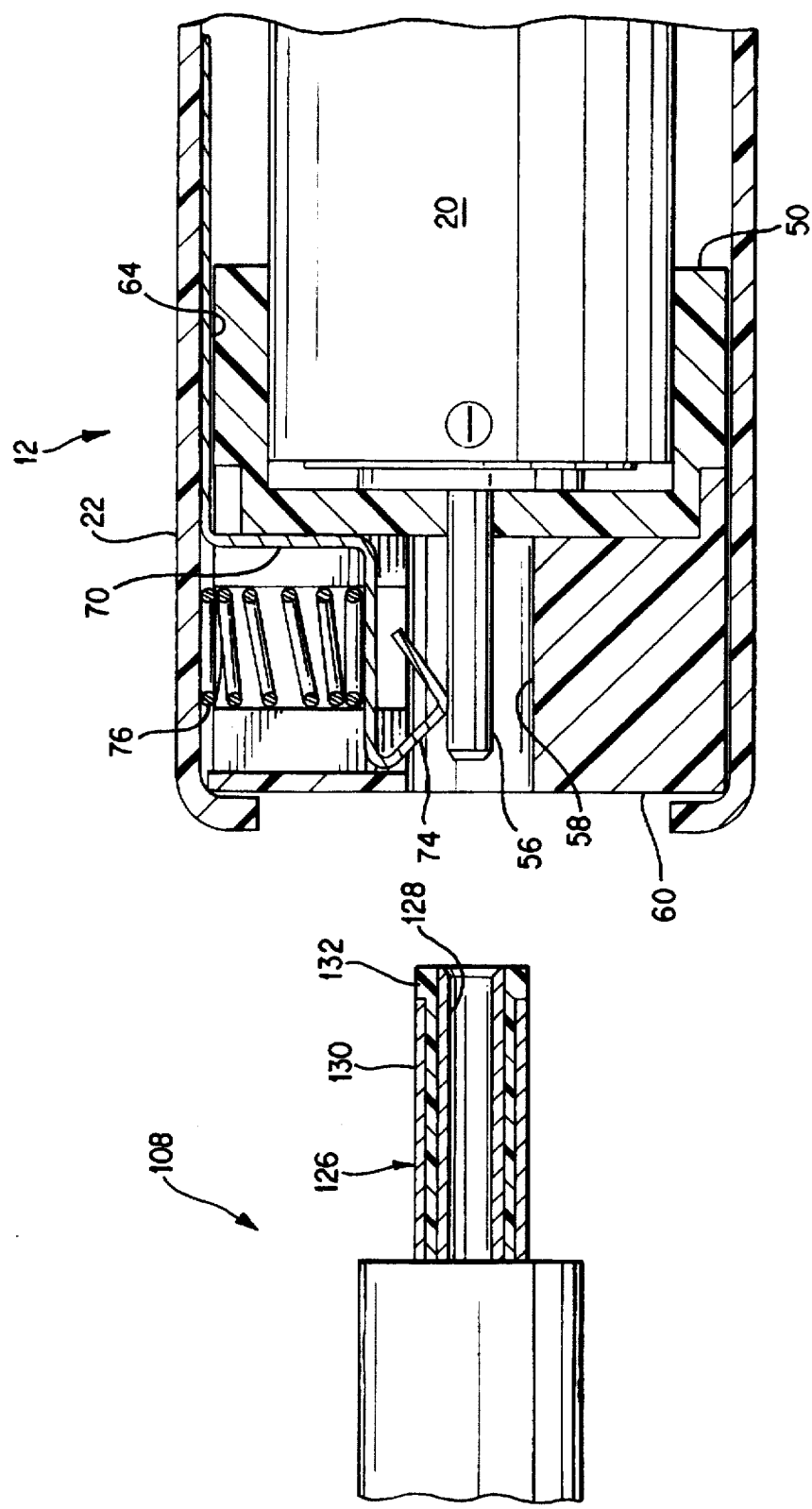
FIG. 8 is a fragmentary side view, partly in section, illustrating assembly of the booster with the handpiece.

Referring now to FIG. 8, it can be seen that booster plug 108 includes a tubular prong 126 having inner and outer conductive surfaces 128 and 130 separated by a tubular insulating sleeve 132. Inner conductive surface 128 has an inner diameter to telescopically receive the pin 56 disposed within the receptacle 58 and is connected to the lead from the positive terminal of battery 104. Outer conductive surface 130 has an outer diameter to fit within the receptacle 58 at the proximal end of the handpiece and is connected to the lead from the negative terminal of the battery 104.

In use, handpiece 12 of the surgical drilling apparatus 10 can be operated alone or with the booster 14 attached. In either case, an appropriate cutting tip 16 is first chosen and then attached to the handpiece by inserting the notched end 90 of the tip into the collet 26 of the handpiece 12 until resistance is felt. The tip 16 is then twisted slightly while continuing to apply axial pressure so that the gap between jaws 80a and 80b of the collet will increase a sufficient amount to allow the notched end 90 of the cutting tip to fit between the jaws and to be held stationary therein due to an inherent inward bias of the jaws. The slim, tapered nose cone 30 and angled tube 28 can be rotated for optimum positioning of the power button 78 and to position the cutting tip 16 at the surgical site. Handpiece 12 can then be used alone by depressing the button 78 to power the motor 18 using only the handpiece battery 20, or the booster 14 can be coupled with the handpiece 12 to increase the voltage applied to motor 18 by connecting battery 104 in series with battery 20.

Coupling of the booster 14 with the handpiece 12 is accomplished by inserting plug 108 of the booster 14 into the receptacle 58 formed at the proximal end of the handpiece 12. As the plug 108 is inserted into the receptacle 58, prong 126 of the plug contacts an angled side of the triangular portion 74 of conductor 62 camming the conductor away from pin 56 against the bias of spring 76. Inner surface 128 of the prong is thus able to slide over the pin 56 thereby connecting the positive terminal of booster battery 104 with the negative terminal of handpiece battery 20. At about the same time, the triangular portion 74 of conductor 62 is biased into contact with outer surface 130 of the prong by spring 76 thereby connecting the negative terminal of the booster battery 104 with the conductor 62. When it is desired to operate the handpiece 12, button 78 is depressed causing the cantilevered portion of the conductor 62 to be deflected inward into contact with the conductive housing 40 of the motor thereby completing the circuit. Since the batteries 20 and 104 are connected in series, however, the voltage applied to the motor 18 is the sum of the voltage of each battery and the operating speed of the motor is thus increased in proportion to the applied voltage. For example, in the case of the Mabuchi model RF-N60CA-13110 motor and 3.5 volt lithium batteries, the operating speed of the drill handpiece is approximately 7000 r.p.m. without the booster attached and approximately 14,000 r.p.m. with the booster attached.

The surgical drilling apparatus 10 described above is particularly useful in otologic and other microsurgical procedures involving both delicate work performed using relatively small burrs (e.g., less than about 1.0 mm) and more aggressive work using larger burrs (e.g., greater than about 1.0 mm) since the handpiece can be used alone for the more delicate aspects of such procedures or with the booster attached for the more aggressive aspects of such procedures. The booster is also useful for providing back-up power or to extend the battery life of the handpiece.

Figure 9:
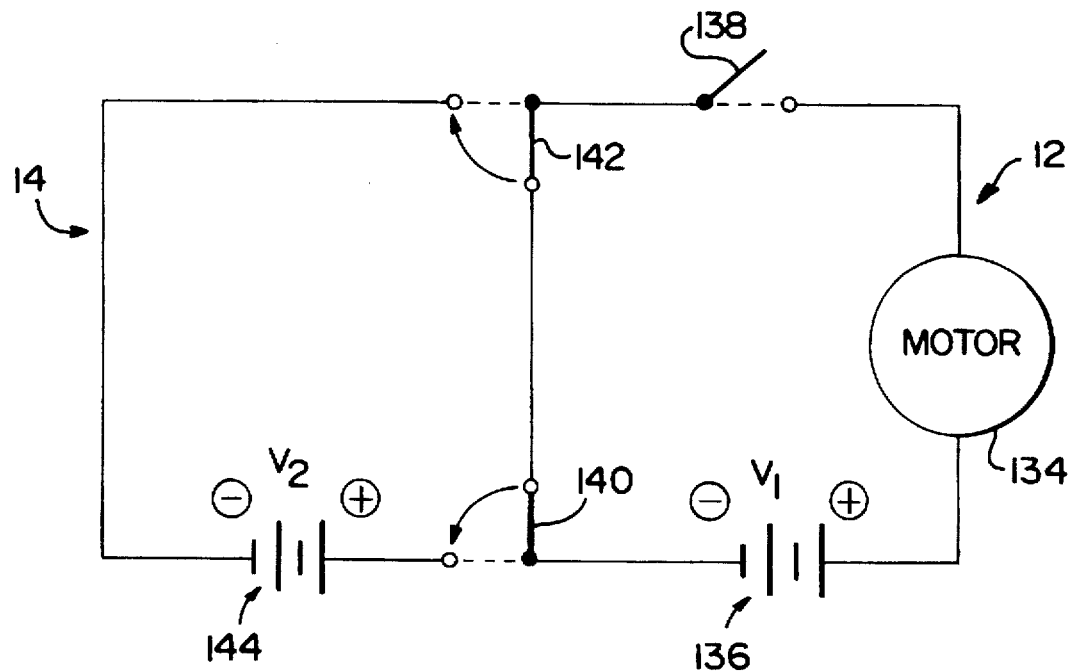
Fig. 9 is an electrical schematic representative of the a connection between the booster and the handpiece.

For purposes of clarity, an electrical schematic diagram representative of the medical instrument according to the present invention is illustrated in FIG. 9. In the diagram, handpiece 12 is depicted as including a motor 134 connected in series with a battery 136 and a single-pole single-throw (SPST) switch 138 that is normally open. In a first, normal position, a pair of single-pole double-throw (SPDT) switches 140 and 142 form part of the conductive path between the battery 136 and the switch 138. With switches 140 and 142 in the first position, shown by solid lines, the circuit is completed by closing switch 138. A voltage $V_1$ is thus applied to the motor. In a second position, caused by assembly of the booster 14 with the handpiece 12, the SPDT switches each assume a second position, shown by broken lines, interrupting the direct connection between the handpiece battery 136 and the SPST switch 138 and placing a booster battery 144 in series with the handpiece battery 136 and the SPST switch 138. As a result, when switch 138 is closed, a voltage of $V_1+V_2$ is applied to the motor causing a change in an operational characteristic of the motor, such as speed or torque.

Figure 10:
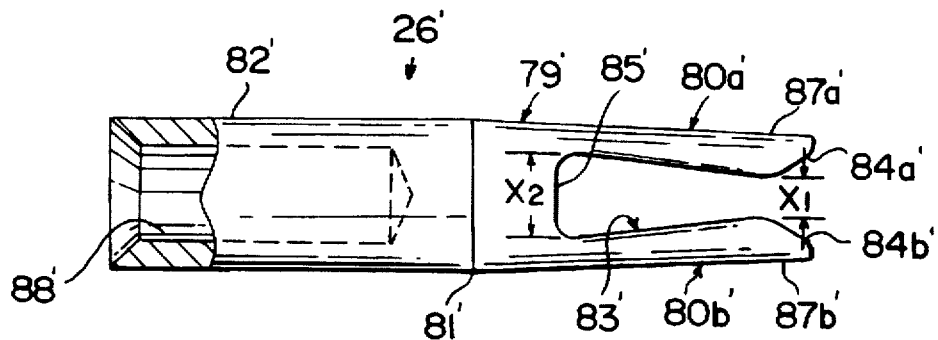
FIG. 10 is a side view of a Modified collet for use with the medical instrument of the present invention.

The components of the medical instrument of the present invention can be modified in various ways to simplify manufacturing and/or to achieve greater precision and reproducibility. For example, in FIG. 10, a modified collet 26' is shown which operates like collet 26 but is formed without the need of having to bend the jaws of the collet after machining. The modified collet 26' includes a cylindrical base 82' with a bore 88' formed at a proximal end thereof and a generally frustoconical jaw portion 79' extending distally from a junction 81' at the distal end of the cylindrical base. Jaw portion 79' defines a pair of laterally opposed jaws 80a' and 80b' separated by a slot 83' of increasing width in the direction of junction 81', the slot defining a first gap $x_1$ near distal ends 84a' and 84b' of the jaws and a second, wider gap $x_2$ at a proximal end 85' of the slot. Outer surfaces 87a' and 87b' of jaws 80a' and 80b' taper radially inward; and, accordingly, the jaws are relatively thin at the proximal end 85' of slot 83' where the gap is widest thereby allowing the jaws to bend near the proximal end of the slot in response to normal insertion pressures. In addition to the above, distal ends 84a' and 84b' adjacent the gap are chamfered or angled outward about 40° relative to a longitudinal axis of the collet to ease insertion of the cutting tip.

In a preferred embodiment, the modified collet 26' is formed of 17–4 stainless steel by electron discharge machining (EDM) of a collet blank having cylindrical and frustoconical portions, the collet blank being heat treated to H-900. After EDM machining, the collet is preferably flash electropolished and ultrasonically cleaned to remove any heat treat scale. The cylindrical base of the modified collet 26' preferably has a diameter of about 0.062 inches and a length of about 0.140 inches, the frustoconical jaw portion 79' having a preferred length of about 0.135 inches and tapering from a diameter equal to that of the base at junction 81' to a terminal diameter of about 0.050 inches. The slot 83' defining the gap between jaws 80a' and 80b' preferably widens from about 0.017 inches at $x_1$ to about 0.034 inches at $x_2$ and has a preferred length of about 0.10 inches.

From the above, it will be appreciated that the medical instrument of the present invention permits modification of an operating characteristic of an electrical device disposed within the handpiece of the medical instrument by attaching a booster having an external DC power source to an internal battery in order to vary the DC voltage applied to the electrical device. By "DC power source" is meant a battery or alternating current (AC) power source that has been converted to DC. When the first DC voltage applied to the electrical device by the internal battery is reduced or inadequate for a particular procedure, attachment of the booster allows a second, larger DC voltage to be applied.

When the medical instrument of the present invention is embodied in a surgical drill, any type of standard motor, battery, drive shaft, collet and cutting tip can be used. The batteries used in the booster and/or handpiece can be conventional dry cell batteries or rechargeable batteries; and, when both the booster and the handpiece include batteries, the batteries can be of the same or different voltages and can be of the same shape and size or of different shapes and sizes depending upon the desired shape and overall size of the medical instrument.

The electrical cable used in connecting the booster with the handpiece is shown and described as being fixed to the booster but can be carried by either the booster or the handpiece and can have any length to permit fixation of the booster at a site remote from the handpiece. Although not shown, the booster can have an adhesive strip, velcro tab or clip mounted on the booster body for attaching the booster to the patient drape or other operating room accessories remote from the surgical site.

The plugs, jacks and switches described herein are merely exemplary and it will be appreciated that other electrical connectors and switches can be used without affecting the function of the medical instrument.

The components of the medical instrument according to the present invention can be made of any medical grade materials. For example, the conductors can be made of any electrically conductive material including, but not limited to, gold, copper, brass, aluminum and platinum. The non-conductive components of the medical instrument, such as the handpiece and booster bodies, can be made of any non-conductive material but are preferably made of a plastic material such as PVC or ABS.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A medical instrument comprising
   a handpiece including a body, an electrical device disposed within said body and having an operating characteristic responsive to DC voltage, and a first battery disposed within said body for applying a first DC voltage to said electrical device to cause said electrical device to operate in a first mode; and
   a booster disposed externally of said body, said booster including a DC power source and means for detachably connecting said DC power source with said first battery to apply a second DC voltage greater than said first DC voltage to said electrical device to cause said electrical device to operate in a second mode;
   wherein said connecting means includes a power cord extending between said booster and said handpiece to permit said booster to be located remotely from said handpiece when said electrical device is operated in said second mode.

2. A medical instrument as recited in claim 1 wherein said DC power source of said booster is a second battery.

3. A medical instrument as recited in claim 2 wherein said second battery is connected in series with said first battery by said connecting means.

4. A medical instrument as recited in claim 3 wherein said booster includes a body and said second battery is disposed within said booster body.

5. A medical instrument as recited in claim 4 wherein said second battery includes positive and negative terminals and said connecting means of said booster includes a plug connected with said terminals.

6. A medical instrument as recited in claim 5 and further comprising a receptacle formed in said handpiece for mating with said plug of said booster in a manner to connect said second battery in series with said first battery.

7. A medical instrument as recited in claim 6 wherein said booster further includes means for attaching said booster body to operating room equipment.

8. A medical instrument as recited in claim 7 wherein said first battery has first and second terminals and further comprising a switch mounted on said handpiece for selectively completing a first conductive path between said first terminal and said electrical device.

9. A medical instrument as recited in claim 8 wherein said first conductive path between said first terminal and said electrical device includes a spring-biased conductor that normally contacts said one terminal.

10. A medical instrument as recited in claim 9 wherein said plug of said booster has a configuration to disconnect said spring-biased conductor from said first terminal of said first battery when inserted into said receptacle in said handpiece while completing a second conductive path from said first terminal through said second battery and to said switch.

11. A medical instrument as recited in claim 1 wherein said electrical device is a motor and said operational characteristic is an operating speed.

12. A medical instrument as recited in claim 11 and further comprising a drive shaft coupled with said motor and a collet disposed at a distal end of said drive shaft.

13. A medical instrument as recited in claim 12 wherein said drive shaft and said collet are disposed within a tube.

14. A medical instrument as recited in claim 13 wherein said collet includes a pair of opposed jaws.

15. A medical instrument as recited in claim 14 and further comprising a cutting tip having a notched end configured to fit between said opposed jaws of said collet in compression.

16. A surgical drilling apparatus for driving cutting tips comprising

> a handpiece including a body, an electrical motor disposed within said body and having an operating speed responsive to DC voltage, a collet coupled with said motor and configured to receive a cutting tip, and a first battery disposed within said body for applying a first DC voltage to said motor to cause said motor to drive the cutting tip in said collet at a first speed suitable for delicate aspects of a surgical procedure; and a booster disposed externally of said handpiece body, said booster including a DC power source and means for detachably connecting said DC power source with said first battery to apply a second DC voltage to said motor to cause said motor to drive the cutting tip in said collet at a second speed greater than said first speed for less delicate aspects of a surgical procedure.

* * * * *